US012232495B2

(12) United States Patent
Guggenbichler

(10) Patent No.: US 12,232,495 B2
(45) Date of Patent: Feb. 25, 2025

(54) METHOD FOR PRODUCING AN ANTIMICROBIAL COMPOSITE MATERIAL AND ANTIMICROBIAL COMPOSITE MATERIAL

(71) Applicant: AMISTEC GMBH & CO. KG, Kössen in Tirol (AT)

(72) Inventor: Joseph-Peter Guggenbichler, Kössen (AT)

(73) Assignee: AMISTEC GMBH & CO. KG, Kössen In Tirol (AT)

( * ) Notice: Subject to any disclaimer, the term of this patent is extended or adjusted under 35 U.S.C. 154(b) by 309 days.

(21) Appl. No.: 15/105,495

(22) PCT Filed: Dec. 19, 2014

(86) PCT No.: PCT/EP2014/078821
§ 371 (c)(1),
(2) Date: Aug. 11, 2016

(87) PCT Pub. No.: WO2015/091993
PCT Pub. Date: Jun. 25, 2015

(65) Prior Publication Data
US 2019/0029259 A1  Jan. 31, 2019

(30) Foreign Application Priority Data
Dec. 19, 2013  (DE) .................... 10 2013 114 575.2

(51) Int. Cl.
| | | |
|---|---|---|
| *A61P 31/04* | (2006.01) | |
| *A01N 25/26* | (2006.01) | |
| *A01N 59/16* | (2006.01) | |
| *A01N 59/20* | (2006.01) | |
| *A01P 1/00* | (2006.01) | |
| *A61L 2/00* | (2006.01) | |
| *A61L 2/232* | (2006.01) | |
| *C08K 3/22* | (2006.01) | |
| *C08K 3/36* | (2006.01) | |
| *C09D 1/00* | (2006.01) | |
| *C09D 5/14* | (2006.01) | |
| *C09D 7/62* | (2018.01) | |
| *C09D 7/63* | (2018.01) | |
| *C08K 5/00* | (2006.01) | |

(52) U.S. Cl.
CPC ............ *A01N 59/16* (2013.01); *A01N 25/26* (2013.01); *A01N 59/20* (2013.01); *A61L 2/232* (2013.01); *C08K 3/22* (2013.01); *C08K 3/36* (2013.01); *C09D 1/00* (2013.01); *C09D 5/14* (2013.01); *C09D 7/62* (2018.01); *C09D 7/63* (2018.01); *C08K 2003/2255* (2013.01); *C08K 2003/2258* (2013.01); *C08K 2003/2296* (2013.01); *C08K 5/0058* (2013.01)

(58) Field of Classification Search
CPC ................ A61K 2300/00; A61K 33/30; A61K 31/7036; A61K 33/24; A61K 31/765; A61K 8/25; A61K 2800/56; A61P 31/04; A01N 59/16; A01N 59/00; A01N 25/26; A01N 25/02; A01N 25/08; A01N 25/12; A01N 61/00; A01N 63/00; A61L 2/00; A01P 1/00; C09D 5/14
See application file for complete search history.

(56) References Cited

U.S. PATENT DOCUMENTS

| | | | |
|---|---|---|---|
| 7,540,906 B2 | 6/2009 | Anderson et al. | |
| 2001/0019727 A1* | 9/2001 | Makita | A01N 59/16 424/646 |
| 2004/0147654 A1* | 7/2004 | Kimura | C08K 9/02 524/403 |
| 2007/0098806 A1* | 5/2007 | Ismail | A61K 9/145 424/489 |
| 2007/0122461 A1* | 5/2007 | Ko | A61K 33/38 424/445 |
| 2010/0057199 A1* | 3/2010 | Guggenbichler | C01G 39/02 604/265 |
| 2011/0124772 A1* | 5/2011 | Wang | A01N 33/12 523/177 |
| 2011/0129514 A1* | 6/2011 | Hossainy | A61B 17/12109 424/423 |
| 2012/0052176 A1* | 3/2012 | Ekanayake | A23B 4/20 426/532 |

(Continued)

FOREIGN PATENT DOCUMENTS

| | | | |
|---|---|---|---|
| CN | 102924951 A | * | 2/2013 |
| DE | 102011085862 A1 | | 5/2013 |

(Continued)

OTHER PUBLICATIONS

Woodford, Chris. Alloys. Feb. 4, 2022. Explain That Stuff. <https://www.explainthatstuff.com/alloys.html>. (Year: 2022).*

Meng, et al., "Preparation of Molybdates with Antibacterial Property", Key Engineering Materials, ISSN: 1662-9795, vols. 368-372, pp. 1516-1518, doi: 10.4028/www.scientific.net/KEM.368-372.1516, online Feb. 11, 2008.

International Search Report corresponding to PCT/EP2014/078821 dated Feb. 13, 2015.

(Continued)

*Primary Examiner* — Tracy Liu
(74) *Attorney, Agent, or Firm* — Tim Tingkang Xia, Esq.; Troutman Pepper Locke

(57) ABSTRACT

The invention relates to a method for producing an antimicrobially effective composite material (10), in which at least one molybdenum and/or tungsten containing inorganic compound is bound to at least one further material. Furthermore, the invention relates to an antimicrobially effective composite material (10), which includes at least one molybdenum and/or tungsten containing compound, which is bound to at least one further material.

15 Claims, 1 Drawing Sheet

(56) References Cited

U.S. PATENT DOCUMENTS

Figure 1:
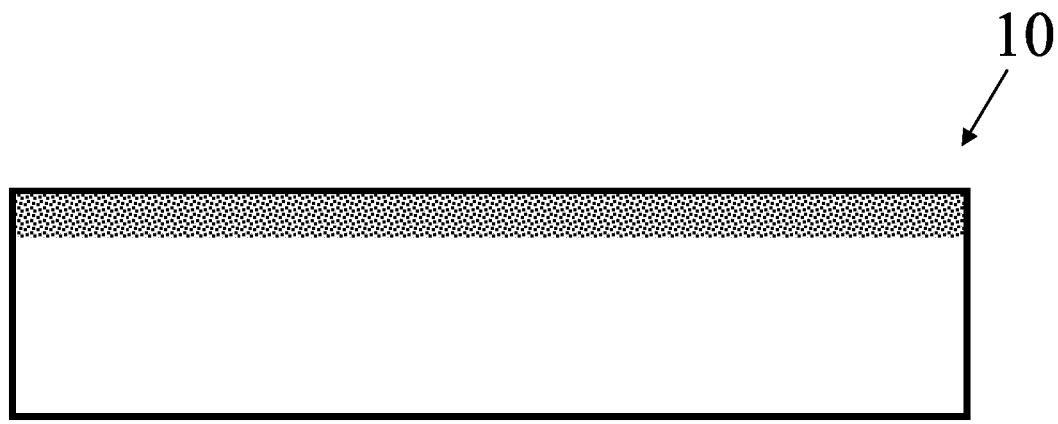

2012/0201861 A1  8/2012  Nakano
2012/0301530 A1* 11/2012  Uhlmann ................ A61P 31/10
                                                    424/405

FOREIGN PATENT DOCUMENTS

| EP | 0111995 | 9/1983 |
| EP | 0882398 | 9/1998 |
| EP | 2255878 A1 | 12/2010 |
| JP | 04288007 A * | 10/1992 |
| WO | WO2008/058707 A2 | 5/2008 |
| WO | WO2010/136792 A2 | 12/2010 |
| WO | WO2013/153124 A1 | 10/2013 |
| WO | WO2014/174084 A1 | 10/2014 |

OTHER PUBLICATIONS

Tetsu Tatsuma et al.: "Bactericidal effect of an energy storage TiO2-WO3 photocatalyst in dark", Electrochemistry Communications, Elsevier, Amsterdam, NL, vol. 5, No. 9, Sep. 1, 2003, pp. 793-796.

Kathrin Lorenz et al.: "Anodic TiO2 nanotube layers electrochemically filled with MoO3 and their antimicrobial properties", BioInterphases, vol. 6, No. 1, Mar. 17, 2011, pp. 16-21.

Cordt Zollfrank et al.: "Antimicrobial activity of transition metal acid Mo0prevents microbial growth on material surfaces", Materials Science and Engineering C, Elsevier Science S.A, CH, vol. 32, No. 1, Sep. 22, 2011, pp. 47-54.

Nathalie Tétault et al.: "Biocidal activity of metalloacid-coated surfaces against multidrug-resistant microorganisms", Antimicrobial Resistance & Infection Control, Nov. 14, 2012, pp. 1-6.

S Shafaei et al: "Molybdenum and tungsten oxides as innovative antimicrobial materials", Book of Abstracts, Nov. 21, 2012, pp. 314-314.

Maximilian Lackner et al: "Polymorphs of molybdenum trioxide as innovative antimicrobial materials", Surface Innovations, vol. 1, No. 4, Oct. 5, 2013, pp. 202-208.

Database WPI, Week 199704, Thomson Scientific, London, GB; Nov. 12, 1996, abstract.

Translation of International Preliminary Report on Patentability dated Jun. 21, 2016, 33 pages.

Lackner, M., et al., *Saure Oberflächen als neuartige Kontaktbiozide*, Nachrichten aus der Chemie, vol. 61, Feb. 2013, 10 pages, Original Document, 4 pages and English Translation by DeepL, 6 pages.

Shafaei, S. et al., *Polymorphs of molybdenum trioxide as innovative antimicrobial materials*, Surface Innovations, vol. 1, Issue S14, Dec. 2013, pp. 202-208.

Zollfrank, C., et al. *Antimicrobial activity of transition metal acid MoO3 prevents microbial growth on material surfaces*, Materials Science and Engineering: C, vol. 32, Sep. 2011, pp. 47-54.

U.S. Appl. No. 12/808,809, filed Nov. 18, 2010.

* cited by examiner

METHOD FOR PRODUCING AN ANTIMICROBIAL COMPOSITE MATERIAL AND ANTIMICROBIAL COMPOSITE MATERIAL

The invention relates to a method for producing an antimicrobially effective composite material, to an antimicrobially effective composite material as well as to the use of such an antimicrobially effective composite material.

Surfaces of items can be antimicrobially equipped according to different methods. Besides organic biocides, metals and metal compounds are often employed for this purpose and employed for antimicrobial equipment of different composite materials. According to the so-called oligodynamic series, a plurality of metal ions is antimicrobially effective, among them for example $Ag^+$, $Cd^{2+}$, $Hg^{2+}$ and $Cu^{2+}$. Silver is particularly often employed besides copper, wherein multiple principal possibilities are known. In the first possibility, the elemental metal is provided with a large surface such that the corresponding metal ions can form on the surface. Therefore, nanoparticles, foamed metal or nanoparticles fixed to a support are often used. The second possibility includes the provision of soluble metal salts, which are for example incorporated in zeolites or directly in the composite material. Furthermore, it is possible to present antimicrobially effective metal ions via the electrochemical series. Hereto, comparatively less noble metals like silver or copper can be galvanically coupled to a more noble metal such as for example platinum.

However, the circumstance is to be considered as disadvantageous in organic biocides that they are dissolved from the composite material as active substances and incorporated into the bacteria metabolism. In addition, in active biocides, there is a high tendency to the development of resistances and cross-resistances. The mentioned noble metals or noble metal ions are comparatively expensive on the one hand and are nearly completely inactivated by sulfur containing compounds as well as by high electrolyte concentrations on the other hand.

It is the object of the present invention to specify a method for producing an antimicrobially effective composite material, which is less expensive and has improved efficacy. Further objects of the invention are in specifying a corresponding antimicrobially effective composite material as well as a use of such a composite material.

According to the invention, the objects are solved by a method having the features of claim 1, an antimicrobially effective composite material having the features of claim 14 as well as by the use of such a composite material specified in claim 15. Advantageous configurations with convenient developments of the invention are specified in the dependent claims.

A first aspect of the invention relates to a method for producing an antimicrobially effective composite material, in which at least one molybdenum and/or tungsten containing inorganic compound is bound to at least one further material. Within the scope of the present invention, a material is understood by a composite material, which is composed of at least two or more substances bound to each other, wherein at least one of the substances is the at least one molybdenum and/or tungsten containing inorganic compound. Therein, further substances of the composite material according to the invention in turn can themselves be composite materials. Since molybdenum and tungsten containing compounds are substantially more inexpensive and exhibit a high antimicrobial effect already in low amounts compared to for example nanosilver, copper, organic biocides and the like, the composite material produced according to the invention can therefore be more inexpensively produced and has improved efficacy. Moreover, molybdenum and tungsten containing compounds are not inactivated by sulfur containing compounds or by high electrolyte concentrations, but keep their efficacy. Although the exact mechanism of the antimicrobial efficacy is not yet conclusively clarified, the applicant assumes that the main effect is achieved in that molybdenum and tungsten containing inorganic compounds transform to molybdic or tungstic acid, oligomolybdates/tungstates and similar acidic molybdenum or tungsten compounds upon contact with water, air humidity etc., which result in decrease of the pH value. Due to this acidic pH value, the adhesiveness of pathogenic germs is a priori severely reduced. Besides reduced adherence of germs, however, reduced strength of the adherence, inhibition of the proliferation, inhibition of the biofilm formation and antimicrobial efficacy are also achieved in already effected biofilm formation. For example, this is of particular importance in hospitals, care homes etc., since microorganisms in the biofilm are not or at least not permanently removable by antibiotics, organic biocides, disinfectants and the like. Since decrease of the pH value is only required in the area of the surface interface of the composite material or a component or product manufactured from it, correspondingly low amounts of molybdenum and/or tungsten containing compounds in the area of the surface are sufficient. Because molybdenum and tungsten containing inorganic compounds are generally poorly to barely water-soluble at least under normal environmental conditions, elution or degradation of the inorganic compounds additionally is omitted such that the antimicrobial efficacy is maintained over the entire lifetime of the composite material in contrast to the prior art. In contrast, active biocides are dissolved from composite materials or from the surfaces thereof with time and incorporated into the bacteria metabolism. Therefore, in active biocides, there is a high tendency to development of resistances and cross-resistances. In contrast, the antimicrobially equipped composite material acts as a passive biocide product, whereby lack of resistance development and resistance induction, respectively, is also ensured besides long-term efficacy. As was further recognized, molybdenum and tungsten containing compounds are not toxic for human beings and animals and thereby have excellent biocompatibility. The at least one further material can basically originate from any material class and be an inorganic, metallic, ceramic and/or organic material. Preferably, the composite material produced according to the invention includes at least one organic polymer or a compound and/or a silicone as the further material. The composite material can basically be formed as a layer composite, fiber composite, particle composite or penetration composite with the aid of the method according to the invention. The composite material produced according to the invention can be solid or liquid under standard conditions. For example, the composite material can be produced in the form of a solution, suspension and/or dispersion, for example as a varnish or liquid coating agent. Basically, it can be provided that the at least one molybdenum and/or tungsten containing compound is at least substantially exclusively disposed in the area of the surface of the composite material, since the antimicrobial effect is to be achieved here. For example, the molybdenum and/or tungsten containing compound can be applied to a substrate or a support material of the composite material as a layer or component of a layer. Therein, only one or multiple areas of the surface or the entire surface of the composite material can basically be antimicrobially equipped. Alternatively or additionally, the at least one molybdenum and/or tungsten containing compound can also be arranged within the composite material and be present distributed in the composite material, respectively. Hereby, the antimicrobial effect can be permanently maintained even upon surface wear of the composite material. Depending on the purpose of use, the composite material can basically be formed as a semi-finished product, that is as a "semi-finished matter" within the scope of the invention, which is only used for its final purpose after further processing steps. Alternatively, the composite material can already be formed as a finished component, which can be used for its respective purpose without further processing steps. Moreover, the composite material produced according to the invention can basically be formed free of elemental molybdenum, $MoO_2$, $MoO_3$, molybdenum carbide, molybdenum nitride, molybdenum silicide or molybdenum sulfide, molybdenum hexacarbonyl, molybdenum acetylacetonate and/or molybdenum containing alloys. The same applies to elemental tungsten and the corresponding tungsten compounds and alloys. In particular, the at least one further substance is not a molybdenum and/or tungsten or not a molybdenum and/or tungsten alloy. Similarly, the composite material can be formed free of non-acid forming metal oxides like zinc oxide, titanium oxide, titanium dioxide, aluminum oxide or other non-acid forming photocatalysts. Furthermore, the method according to the invention can basically be performed without the use of additional antimicrobially effective compounds such as for example silver, in particular nanosilver, or silver compounds, in particular soluble silver compounds as silver nitrate and the like, copper, organic biocides, zeolites or the like in contrast to the prior art, whereby considerable cost reductions are also given besides better environmental compatibility of the composite material produced according to the invention.

In an advantageous configuration of the invention, it is provided that at least one molybdenum and/or tungsten containing inorganic compound is used, which is doped and/or undoped and/or free of water of crystallization and/or containing water of crystallization. Within the scope of the present invention, the incorporation of foreign atoms into the molybdenum containing compound is understood by doping, whereby optimum adaptability of the antimicrobial effect to different purposes of employment and requirement profiles is allowed. Therein, the amount of foreign atoms is basically between about 0.1 and 1000 ppm, preferably between 100 ppm and 600 ppm, in particular between 300 ppm and 550 ppm. Alternatively or additionally, both molybdenum compounds free of water of crystallization and hydrates, that is monohydrates, dehydrates, trihydrates etc., of the inorganic molybdenum compounds according to compound can be used individually or in any combination. Similarly, the at least one inorganic molybdenum compound can be present in any crystal configuration or crystal lattice structure, as a mixed crystal and/or in amorphous manner.

In a further advantageous configuration of the invention, it is provided that $MO_{3-x}$ with M=Mo and/or W and $0<x<1$ is used as the inorganic compound. In other words, it is provided that an oxide deficient in oxygen with respect to $MoO_3$ and/or $WO_3$ is used as the inorganic compound, the oxygen content of which is between those of $MoO_3/WO_3$ and $MoO_2/WO_2$. Accordingly, x can for example take values of 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or 0.99 as well as all of the possible intermediate values. With the aid of these compounds, individually or in any combination, a surface pH value as low as possible and thereby a particularly good antimicrobial efficacy are achieved in particularly simple and inexpensive manner, since all of the mentioned compounds transform to molybdic and tungstic acid, respectively, and/or higher acidic oligomolybdates and oligotungstates, respectively, upon contact with water. Moreover, the mentioned compounds have a comparatively high oxidation potential, magnetic characteristics and/or electrical conductivity due to the different oxidation stages of Mo/W, that is substantially +IV, +V and/or +VI, whereby additional antimicrobial effects can be achieved.

The compounds of the general formula $MO_{3-x}$ can be particularly simply and inexpensively produced by partial oxidation of M and/or $MO_2$ and/or by partial reduction of $MO_3$. In other words, the metals Mo/W and/or the dioxides $MoO_2/WO_2$ can be oxidized to arrive at the compounds of the general formula $MO_{3-x}$. Alternatively or additionally, the respective trioxides $MoO_3$ and/or $WO_3$ can be used as educts and be partially reduced.

In a further advantageous configuration of the invention, it is provided that the compound $MO_{3-x}$ is produced by means of a fluidized bed reactor and/or by chemical vapor deposition and/or by physical vapor deposition and/or by sputtering and/or plasma-assisted and/or in a controlled atmosphere. The use of a fluidized bed reactor offers various advantages. On the one hand, the preferably particulate educts can be set in a fluidized state with a fluid in controlled manner, wherein a reactive gas or gas mixture can for example be used as the fluid, by means of which the partial oxidation and/or reduction can be performed. Alternatively or additionally, a desired reaction temperature can be adjusted via the fluid. Similarly, the fluidized educts can be passed past an energy source, for example a flame and/or a plasma source, by a corresponding fluid flow, for example in annular manner, whereby the contact time for the individual particles and thereby their oxidation or reduction degree can be particularly precisely adjusted. Similarly, the educt flow can be specifically mixed with a reactant or reactant mixture or be passed past a reactant flow. Furthermore, further functionalizations of the inorganic molybdenum and/or tungsten compounds can be performed in addition to the oxidation and reduction, respectively, with the aid of the fluidized bed reactor. For example, the molybdenum and/or tungsten compounds can be provided with a functional layer, for example a reactant layer, a hydrophilizing layer and the like before, during and/or after the oxidation and reduction, respectively. With the aid of chemical and/or physical vapor deposition, the composite material according to the invention can advantageously be immediately produced by directly coating the at least one further material with the molybdenum and/or tungsten containing compound. Corresponding advantages arise upon layer application by means of sputtering. Furthermore, it can be provided that the reaction is controlled by adjusting a controlled atmosphere. For example, a reduction can occur in a controlled hydrogen atmosphere, while for example oxygen, ozone, hydrogen peroxide, chlorine or other oxidative compounds can be used individually and in any combination for adjusting oxidative conditions. However, a wet-chemical production is basically also possible.

In a further advantageous configuration of the invention, it is provided that at least one molybdate and/or tungstate and/or a compound of the chemical formula $A^{n+}{}_zMO_4$, in which M denotes Mo and/or W, A denotes at least one metal ion different from Mo and W and/or $NH_4^+$ and n*z=+2, is used as the inorganic compound. By the use of one or more of the mentioned compounds, besides good antimicrobial efficacy, a particularly high light stability, in particular with respect to UV light, is surprisingly also achieved. Thus, the occurrence of undesired discolorations on the surface of the composite material produced according to the invention or a component produced therefrom is particularly reliably prevented. Moreover, such molybdates and tungstates have a particularly low water solubility and are at least substantially colorless or white. Hereby, the composite material produced according to the invention is particularly well suited for production of items, for which a neutral, white surface is desired. In reverse, however, simple coloration can also be performed by the addition of corresponding colorants or color pigments due to the neutral-white color of the surface.

In further configuration of the invention, it has appeared advantageous if A of the chemical formula $A^{n+}{}_zMO_4$ is selected from a group including Na, K, Mg, Ca, Ag, Cu, Bi, V, Ti and Zn. Hereby, the solubility, the color and the antimicrobial efficacy of the composite material can be optimally adapted to its respective purpose of employment. In addition, with the aid of the mentioned compounds, individually and in any combination, the adhesion of microorganisms to the surface of the composite material can additionally be impeded. This particularly effectively prevents the colonization of the surface of the composite material. The mentioned molybdates and/or tungstates can be particularly fast, simply and inexpensively produced by commonly heating the desired carbonates, for example $Na_2CO_3$, $ZnCO_3$, $CaCO_3$ etc., with $MoO_3$ and/or $WO_3$.

In a further advantageous configuration of the invention, it is provided that a molybdenum and/or tungsten containing inorganic mixed compound is used as the inorganic compound. Due to the similar atomic radii of molybdenum and tungsten, both elements can often be partially or completely exchanged to each other in compounds. Such molybdenum-tungsten mixed compounds usually have a considerably lower water solubility than the respective molybdenum and tungsten pure compounds, respectively, without the antimicrobial efficacy degrading. Thus, elution of the antimicrobial active agent is particularly reliably prevented such that the composite material produced according to the invention is particularly well suitable for the production of products and items, which have to be frequently cleaned and are in frequent contact with water, respectively.

In a further advantageous configuration of the invention, it is provided that the molybdenum and tungsten containing mixed compound is doped with a fluorine compound, in particular with an oxyfluoride, WOF4, $WO_2F_2$, calcium fluoride and/or fluorapatite. Hereby too, the antimicrobial efficacy can be advantageously improved and be optimally adapted to the respective purpose of employment of the composite material. Doping with a fluorine compound offers the additional advantage that the adhesion of microorganisms to the surface of the mixed oxide is additionally impeded. Thus, this prevents the colonization of surfaces provided with the mixed oxide and thereby additionally improves the antimicrobial effect. Herein, fluorine compounds with a water solubility as low as possible are preferably used to also prevent or at least slow down elution. Non-exhaustive examples for suitable compounds are calcium fluoride ($CaF_2$) and fluorapatite ($Ca_5[F](PO_4)_3$). The use of $WOF_4$, $WO_2F_2$ and/or corresponding molybdenum oxyfluorides offers the additional advantage that they contribute to the production of the mixed oxide and to the doping thereof with fluoride ions or fluorine compounds at the same time.

Alternatively or additionally, it is provided that a mixed oxide of the chemical formula $Mo_xW_{1-x}A_yO_z$ is used as the molybdenum and tungsten containing inorganic mixed compound, in which $0<x<1$, $0 \leq y \leq 2$ and $2.0 \leq z \leq 3.0$ and A denotes a metal ion different from Mo and W and/or $NH_4^+$. Thus, the parameter x can for example take values of 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or 0.99 as well as corresponding intermediate values. Accordingly, the parameter y can for example take values of 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00 as well as corresponding intermediate values. The parameter z can for example take values of 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99 or 3.00 as well as corresponding intermediate values. Hereby, the antimicrobial, optical, physical and chemical characteristics of the composite material can be optimally adapted to its respective configuration and its respective purpose of employment In the simplest configuration (y=0), the mixed oxide can only contain Mo, W, O and optionally voids in the crystal lattice and be undoped. Alternatively, the mixed oxide can be doped. As already mentioned, the mixed oxide can also contain one or more metal ions different from Mo and W and/or ammonium ions within the limits defined by y besides Mo, W and O. Furthermore, it can be provided that multiple different mixed oxides or a heterogeneous mixed oxide with components varying within the indicated chemical formula are used.

In a further advantageous configuration of the invention, it is provided that A is selected from a group including Na, K, Mg, Ca, Ag, Cu, Bi, V, Ti and Zn. Hereby, the solubility, the color and the antimicrobial efficacy of the composite material can be optimally adapted to its respective purpose of employment. In addition, with the aid of the mentioned compounds, individually and in any combination, the adhesion of microorganisms to the surface of the composite material can additionally be impeded. This particularly effectively prevents the colonization of the surface of the composite material.

Further advantages arise in that the at least one molybdenum and/or tungsten containing inorganic compound is used in the form of particles with an average grain size between 0.1 μm and 200 μm and/or that the mass content of the at least one molybdenum and/or tungsten containing compound related to the total mass of the composite material is between 0.1% and 80%, in particular between 1.5% and 30% and preferably between 1.8% and 5.0%. Hereby, a particularly high antimicrobial efficacy is ensured with matter input as low as possible of molybdenum and/or tungsten containing compounds. In addition, the performance of the method can be optimally adapted to the later purpose of employment of the composite material. The use of particles with the mentioned average grain sizes offers the particular advantage that a particularly high antimicrobial efficacy can be realized on the one hand and that the composite material produced according to the invention can be produced free of nanoparticles on the other hand. By an average grain size between 0.1 μm and 200 μm, in particular average grain sizes of 0.10 μm, 0.20 μm, 0.30 μm, 0.40 μm, 0.50 μm, 0.60 μm, 0.70 μm, 0.80 μm, 0.90 μm, 1.00 μm, 1.10 μm, 1.20 μm, 1.30 μm, 1.40 μm, 1.50 μm, 1.60 μm, 1.70 μm, 1.80 μm, 1.90 μm, 2.00 μm, 2.10 μm, 2.20 μm, 2.30 μm, 2.40 μm, 2.50 μm, 2.60 μm, 2.70 μm, 2.80 μm, 2.90 μm, 3.00 μm, 3.10 μm, 3.20 μm, 3.30 μm, 3.40 μm, 3.50 μm, 3.60 μm, 3.70 μm, 3.80 μm, 3.90 μm, 4.00 μm, 4.10 μm, 4.20 μm, 4.30 μm, 4.40 μm, 4.50 μm, 4.60 μm, 4.70 μm, 4.80 μm, 4.90 μm, 5.00 μm. 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 51 μm, 52 μm, 53 μm, 54 μm, 55 μm, 56 μm, 57 μm, 58 μm, 59 μm, 60 μm, 61 μm, 62 μm, 63 μm, 64 μm, 65 μm, 66 μm, 67 μm, 68 μm, 69 μm, 70 μm, 71 μm, 72 μm, 73 μm, 74 μm, 75 μm, 76 μm, 77 μm, 78 μm, 79 μm, 80 μm, 81 μm, 82 μm, 83 μm, 84 μm, 85 μm, 86 μm, 87 μm, 88 μm, 89 μm, 90 μm, 91 μm, 92 μm, 93 μm, 94 μm, 95 μm, 96 μm, 97 μm, 98 μm, 99 μm, 100 μm, 101 μm, 102 μm, 103 μm, 104 μm, 105 μm, 106 μm, 107 μm, 108 μm, 109 μm, 110 μm, 111 μm, 112 μm, 113 μm, 114 μm, 115 μm, 116 μm, 117 μm, 118 μm, 119 μm, 120 μm, 121 μm, 122 μm, 123 μm, 124 μm, 125 μm, 126 μm, 127 μm, 128 μm, 129 μm, 130 μm, 131 μm, 132 μm, 133 μm, 134 μm, 135 μm, 136 μm, 137 μm, 138 μm, 139 μm, 140 μm, 141 μm, 142 μm, 143 μm, 144 μm, 145 μm, 146 μm, 147 μm, 148 μm, 149 μm, 150 μm, 151 μm, 152 μm, 153 μm, 154 μm, 155 μm, 156 μm, 157 μm, 158 μm, 159 μm, 160 μm, 161 μm, 162 μm, 163 μm, 164 μm, 165 μm, 166 μm, 167 μm, 168 μm, 169 μm, 170 μm, 171 μm, 172 μm, 173 μm, 174 μm, 175 μm, 176 μm, 177 μm, 178 μm, 179 μm, 180 μm, 181 μm, 182 μm, 183 μm, 184 μm, 185 μm, 186 μm, 187 μm, 188 μm, 189 μm, 190 μm, 191 μm, 192 μm, 193 μm, 194 μm, 195 μm, 196 μm, 197 μm, 198 μm, 199 μm or 200 μm are to be understood. Alternatively or additionally, the mass content of the at least one molybdenum and/or tungsten containing compounds related to the total mass of the composite material can for example be 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% or 80%. Furthermore, it can be provided that the mass portion of all of the molybdenum and/or tungsten containing compounds in the composite material related to the total mass of the composite material is between 0.1% and 80%.

Further advantages arise by arranging at least one hydrophilizing and/or hygroscoping agent at least in the area of the surface of the composite material in addition to the at least one molybdenum and/or tungsten containing inorganic compound. Hereby, the antimicrobial efficacy of the composite material produced according to the invention is advantageously increased in particularly dry environments, that is for example with very low air humidity and accordingly low available amounts of water, which are important for forming an acidic surface interface. Basically, the hydrophilizing and/or hygroscoping agent can be processed together with or separately from the at least one molybdenum and tungsten containing compound, respectively. Examples for suitable hydrophilizing and/or hygroscoping agents are organic acids such as abietic acid, arachidonic acid, arachidic acid, behenic acid, capric acid, caproic acid, cerotic acid, erucic acid, fusaric acid, fumaric acid, bile acids, icocenic acid, isophthalic acid, lactone acid, lauric acid, lignoceric acid, linolenic acid, levopimaric acid, linoleic acid, margaric acid, melissic acid, montanic acid, myristic acid, neoabietic acid, nervonic acid, nonadecanoic acid, oleic acid, palmitic acid, palmitoleic acid, pelargonic acid (nonanoic acid), pimaric acid, palustric acid, palmitic acid, ricinoleic acid, stearic acid, sorbic acid, tannic acid, tridecanoic acid, undecanoic acid and vulpinic acid. Furthermore, malonic acid, maleic acid and maleic anhydride, lactic acid, acetic acid, citric acid, salicylic acid and ascorbic acid (vitamin C) as well as the salts thereof have proven advantageous. Acid anhydrides, ampholytic substances, buffer systems, polymeric acids, ion exchange resins as well as acid sulfonates and acid halides can also be provided. The use of acids as hydrophilizing and/or hygroscoping agent offers the additional advantage that the transformation of the at least one molybdenum and/or tungsten containing compound to molybdic acid or tungstic acid and higher Mo/W acid condensates is promoted. However, it is to be emphasized that other hydrophilizing and/or hygroscoping agents can basically also be used. For example, silica gels, pyrogenic silica (fumed silica) and zeolites, individually and in any combination, are also suitable as hydrophilizing and/or hygroscoping agents since they form a kind of humidity buffer. Preferably, micronized silica gels with particle size distributions in the range between 0.1 μm and 25 μm of average particle diameter are used. Thereby, a minimum residual humidity in the product can be varied and adjusted in wide ranges. Further suitable hydrophilizing and/or hygroscoping agents include the compounds available under the trade names Crodamide ER/BR (fatty amides), Hostastat (ethoxylated alkylamines), Crodafos MCA-SO (solid cetyl phosphate esters), Lubrophos LM-400E (ethoxylated nonylphenol phosphates), Pluronic PE 8100 (non-ionic surfactants, block copolymers, in which the central polypropylene glycol group is flanked by two polyethylene glycol groups), Surfynol 440 (ethoxylated wetting agent), Orevac PP CA100 (chemically functionalized polypropylene with high content of grafted maleic anhydride), Crodamol OHS (propylene glycol polyethylene glycol-3-isocetylether acetate), Pluronic PE 8100 (non-ionic surfactant), Flerol KFC (polyglycolether), BYK P4100 (copolymer with acid groups, which is free of silicones and waxes), Disperplast 1150 (polar, acidic ester of long-chain alcohols), Disperplast 1018 (copolymer with pigment-affine groups), Atmer 129 MB (vegetable glycerol ester) and Palsgaard DMG0093 (emulsifier based on distilled monoglycerides of vegetable fatty acids), which can be used individually and in any combination.

Further advantages arise if the mass content of the hydrophilizing and/or hygroscoping agent related to the total weight of the composite material is between 0.1% and 15%. For example, the mass content can be 0.1%, 0.5%, 1%, 2%, 3%, 4%, 5%, 6%, 7%, 8%, 9%, 10%, 11%, 12%, 13%, 14% or 15%. In particular, a mass content can be chosen, which is between 1% and 5%, in particular in the range of 2% to 4%. Furthermore, the mass content or the mass ratio of the hydrophilizing and/or hygroscoping agent can be chosen such that it corresponds to the selected mass content of the molybdenum compound. For example, 2% of the hydrophilizing and/or hygroscoping agent can be used if the mass content of the molybdenum containing compound related to the weight of the composite material is also 2%. Alternatively, the mass content of the hydrophilizing and/or hygroscoping agent can be about twice as much as the mass content of the molybdenum compound. For example, 4% of hydrophilizing and/or hygroscoping agent can be used if the mass content of the molybdenum containing compound is 2%.

Furthermore, it can be provided that the at least one molybdenum and/or tungsten containing compound is at least partially coated and/or agglomerated with the hydrophilizing and/or hygroscoping agent. Hereby, spatial proximity of the two compound classes is ensured in simple manner such that the molybdenum and/or tungsten containing compound is immediately supplied with the humidity required for lowering the pH value even under particularly dry conditions.

A second aspect of the invention relates to an antimicrobially effective composite material, wherein it is provided according to the invention that it includes at least one molybdenum and/or tungsten containing inorganic compound, which is bound to at least one further material. Thereby, the composite material according to the invention is particularly inexpensively producible and has improved efficacy. Further features and the advantages thereof can be taken from the descriptions of the first inventive aspect, wherein advantageous configurations of the first inventive aspect are to be regarded as advantageous configurations of the second inventive aspect and vice versa.

A third aspect of the invention relates to the use of an antimicrobially effective composite material, which is obtainable and/or obtained by means of a method according to the first inventive aspect and/or is formed according to the second inventive aspect, for producing an antimicrobially effective product. The product obtained using the antimicrobially effective composite material is thereby particularly inexpensively producible and has improved efficacy. Further features and the advantages thereof can be taken from the descriptions of the first and the second inventive aspect, wherein advantageous configurations of the first and the second inventive aspect are to be regarded as advantageous configurations of the third inventive aspect and vice versa.

Figure 2:
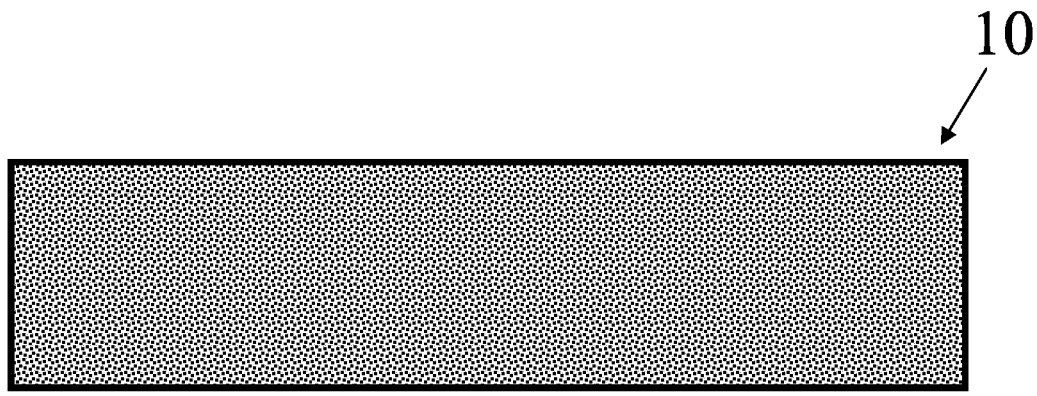

Further features of the invention are apparent from the claims, the embodiments as well as based on the drawings. The features and feature combinations mentioned above in the description as well as the features and feature combinations mentioned below in the embodiments are usable not only in the respectively specified combination, but also in other combinations without departing from the scope of the invention. There shows:

FIG. 1 a schematic sectional view of an antimicrobially effective composite material, which includes a molybdenum containing inorganic compound in the area of its surface; and FIG. 2 a schematic sectional view of a further antimicrobially effective composite material, which includes a tungsten containing inorganic compound.

In a first embodiment, the molybdates $CaMO_4$, $ZnMO_4$, $BiMO_4$, $VMO_4$, $CuMO_4$ and $Ag_2MO_4$ with M=Mo, W are produced by intimately mixing $MoO_3$ and/or $WO_3$ with the corresponding carbonates, for example $CaCO_3$, $MgCO_3$, $ZnCO_3$, $BiCO_3$ etc. in equimolar ratios and heating the mixture to temperatures of about 400° C. to 800° C. Therein, different carbonates can basically also be used to obtain corresponding mixed molybdates and mixed tungstates, respectively. The reaction can be driven towards the desired products by removing the arising $CO_2$. As soon as carbonate is no longer detectable, the conversion has completely occurred. Alternatively, various molybdates/tungstates can be produced by dripping a metal salt solution—e.g. an $AgNO_3$ solution—to a $Na_2MoO_4$ and $Na_2WO_4$ solution, respectively, with subsequent separation of the formed molybdate/tungstate precipitation. The precipitation can then be washed and dried as needed. This variation of production puts itself forward in cases, in which the formed molybdate/tungstate has a lower water solubility than $Na_2MoO_4$ and $Na_2WO_4$, respectively, and than the used metal salt. Besides a good antimicrobial effect, the mentioned compounds also exhibit particularly high light and UV stability. The examination of the UV resistance can be performed in accordance with DIN EN 438-2, section 27. Herein, a sample of a composite material is produced by binding one or more of the mentioned molybdates and tungstates, respectively, to a further material. Therein, the molybdates and tungstates, respectively, can be present as a layer or component of a layer and/or be present distributed in the at least one further material. The composite material is exposed to radiation for 60 minutes. The same is effected with a comparative sample ("standard product") produced in analogous manner, but without addition of the molybdenum/tungsten compounds.

The evaluation is then effected based on a visual comparison of the antimicrobially equipped and the non-equipped sample and is for example evaluated as follows:
1: no perceptible difference to the standard product
2: hardly perceptible difference to the standard product
3: uniquely perceptible difference to the standard product
4: just acceptable difference to the standard product
5: non-acceptable difference to the standard product Therein, values of 1 or at most 2 are always obtained for the mentioned molybdates/tungstates.

The same experiments were performed with compounds of the general formula $MO_{3-x}$ with $0<x<1$ and M=W, Mo. Hereto, $MoO_2$ and $WO_2$ were partially oxidized individually or in certain mixture ratios or $MoO_3$ and/or $WO_3$ were partially reduced. The resulting oxides or mixed oxides also had excellent antimicrobial characteristics if they were present as a composite material with at least one further material. Examples for this are $MoO_{2.35}$ to $MoO_{2.97}$ and $WO_{2.35}$ to $WO_{2.97}$.

As further materials, for example plastics, paints, varnishes, silicones, gum, rubber, melamine, acrylates, methacrylates, waxes, epoxy resins, glass, metal, ceramic and further are basically possible. The material, into which the molybdenum and tungsten compound(s) is or are incorporated, respectively, for the purpose of antimicrobial equipment, can form a solid and/or liquid matrix. It can be provided that the molybdenum and tungsten compounds, respectively, are added such that they constitute between 0.1% and 10% (percent by weight or volume) of the total weight or total volume. Furthermore, it can be provided that the molybdenum and tungsten compounds, respectively, are used in particulate form with average particle sizes between 0.1 μm and 100 μm.

For example, the at least one further material can include or consist of hydrophobic polymers such as silicones, polypropylene (PP), acrylonitril-butadiene-styrene (ABS), polycarbonate (PC) or polystyrene (PS). Phenolic resins, phenol formaldehyde resins, melamine resins, melamine formaldehyde resins, urea resins, urea formaldehyde resins and polymeric diphenylmethane diisocyanate as well as any mixtures therefrom can also be provided. Furthermore, the composite material can include polyethylene (PE), polyethylene terephthalate (PET), polyvinylchloride (PVC), polystyrene (PS), polycarbonate (PC) or a poly(meth)acrylate (e.g. PAA, PAN, PMA, PBA, ANBA, ANMA, PMMA, AMMA, MABS and/or MBS) as a further material. The use of thermoplastic elastomers allows production of surfaces with rubbery-elastic characteristics, in which the at least one molybdenum/tungsten containing compound is received or retained. The thermoplastic elastomer(s) can for example belong to the classes of TPO, TPV, TPU, TPC, TPS or TPA or any mixtures hereof, wherein thermoplastic elastomers based on urethane (TPUs) have in particular proven advantageous. The use of a reactive varnish allows production of mechanically particularly resistive surfaces, wherein the reactive varnish preferably already cures at room temperature by chemical reaction. Basically, the reactive varnish can be present or used as a one- or multi-component varnish. Similarly, the composite material can basically be formed as a UV-curable varnish, acrylic varnish and/or silicone containing varnish. In case of the configuration as an UV-curable varnish, the use of light- and/or UV-stable molybdenum/tungsten containing compounds has proven advantageous to avoid discolorations. However, in reverse, light- and UV-labile molybdenum/tungsten containing compounds, respectively, can also be used and be converted at the same time with curing of the varnish. Composite material varnishes based on silicone have the advantage of a very low change of their film volume during curing due to their low portion of organic groups. Hereby, very dense layers with good film strength can be produced, in which the at least one molybdenum/tungsten containing compound is received or retained. Moreover, silicone varnishes have a high thermal resistance and are therefore suitable for coating of items, which are provided for use in the area of heat sources.

FIG. 1 shows a schematic sectional view of an antimicrobially effective composite material 10 for further illustration, which includes $ZnMoO_4$ as a molybdenum containing inorganic compound only in the area of its surface. Therein, the $ZnMoO_4$, which is illustrated dotted, is present with a mass portion of 2% in polypropylene (PP). The $ZnMoO_4$ containing surface area preferably forms an outer side of a product produced of the composite material 10.

FIG. 2 shows a schematic sectional view of a further antimicrobially effective composite material 10, which includes $WO_{2.97}$ as a tungsten containing inorganic compound 12. One recognizes that the tungsten oxide is present not only on the surface, but finely distributed in the entire volume of the composite material 10 in contrast to the preceding example, wherein a PP matrix was again used as a further material.

As further embodiments, the following composite materials were produced, which all exhibited an excellent antimicrobial efficacy:

PP+2% $WO_{3-x}$(blue)+2% silica gel

PP+2% $WO_3$(yellow)+2% silica gel

PP+2% $MoO_3$+2% silica gel+2% Atmer

PP+2% $ZnMoO_4$+2% silica gel+2% Atmer

PP+4% $ZnMoO_4$

PP+4% $MoO_3$

PP+4% $WO_{3-x}$(blue)

PP+4% $WO_{3-x}$(blue)+2% silica gel

PP+4% $WO_3$(yellow)+2% silica gel

PP+4% $WO_3$(yellow)+2% silica gel

Therein, silica gel and Atmer function as hydrophilizing and hygroscoping agents, respectively.

For production, the molybdenum and tungsten compounds, respectively, as well as optionally the hydrophilizing and hygroscoping agents, respectively, were mixed in powdered form with average particle diameters between 0.1 μm and 5 μm into the PP in a Brabender Plasticorder. It is to be emphasized that other plastics such as for example PE, TPU, PU and the like can basically also be used. Furthermore, besides die casting, injection molding materials can also be antimicrobially equipped. The same applies to composite materials, which include inorganic materials as a matrix besides molybdenum/tungsten containing compounds.

The individual samples were sprayed with water about 3 hours before the first test of the antimicrobial efficacy to ensure a sufficient residual humidity in the composite material 10. The test for antimicrobial efficacy was effected after drying on dry surface. Hereto, the individual, dried composite materials were first contaminated with a germ suspension (germ number $10^6$). *Staphylococcus aureus* (s.a.), *Pseudomonas* aeruginosa (p.a.) and *Escherichia coli* (*E. coli*) were used as germs. The respective concentration of the germ suspension was determined and adjusted via photometric measurement.

Each 10 μl of the germ suspension was applied to the composite material 10 with the aid of a pipette and streaked with a Drigalski spatula. After complete drying of the germ suspension (after about one hour without further contact or treatment), so-called contact tests were performed after 0, 3, 6 and 9 hours. Hereto, a Caso agar contact plate is pressed onto the contaminated surface area and thereafter incubated for 24 hours in a manner known per se. In the composite materials 10, germ growth could no longer be ascertained usually after 3 hours, but at the latest after 6 hours. Corresponding results could also be achieved with the dripping method known per se.

The antimicrobial efficacy could be maintained over several weeks in very dry environments with air humidity values below 20% even in those composite materials 10 without hydrophilizing and hygroscoping agent, respectively. However, the use of hydrophilizing and hygroscoping agent, respectively, improves, but in particular extends the antimicrobial efficacy under very dry conditions. At very low air humidity values, the antimicrobial efficacy can be again regenerated after some days by new wetting, for example by wiping the surface with a wet cloth. At higher air humidities above about 30%, particular measures are not required to permanently maintain the antimicrobial efficacy.

The composite material 10 can be used for producing very different products and items. The product can for example be formed as an implant, catheter, stent, bone implant, dental implant, vascular prosthesis, endoprosthesis, exoprosthesis, cable, hose, food packaging, container, fuel tank, household product, counter, fitting, keyboard, mouse, joystick, housing, textile, item of clothing, furniture and/or interior construction part, household appliance, credit card, mobile phone case, coin, bill, door handle, refrigerator, trickling material in the cooling tower, varnish coating, tile or a part of the interior fittings of a building or public service vehicle. Furthermore, it can be provided that the product is formed as a storage and transport container or as a conduit for hydrocarbons, fuels, solvents and organic liquids. Similarly, the composite material according to the invention can be used for producing an item from the group of the housewares, medical technology, food engineering, sanitary installations, packagings, textiles, clinics, counters, seats and keyboards. Similarly, it is suitable for products being in frequent touch contact with living beings. A further advantageous use is in components for air conditioning systems. The cooling fins, which are usually composed of a Cu or Al alloy, can be advantageously coated with the composite material according to the invention or be produced from it. The ducts of air conditioning systems in buildings can also be antimicrobially configured by adding the composite material 10 to the duct material, coating the duct material with them or if the duct material is composed of the composite material 10. Air humidifiers can also be provided with corresponding antimicrobial characteristics. In addition, the composite material can be used in cables and/or for producing cables.

In further configuration of the invention, the composite material is formed as a coating agent, in particular as a paint, varnish and/or antifouling coat. Embodiments of the composite material are understood by a paint, which have a liquid to pasty consistency and result in a physically or chemically dry coat applied to surfaces. Hereby, the advantageous characteristics of the composite material according to the invention can be particularly flexibly realized for any items and surfaces. Important configurations are for example antifouling coats, e.g. for ships, as well as antimicrobial equipment in the health system, the industry, the food sector and the private sector.

In a further embodiment, at least the surface of the composite material is hydrophilized. Here, hydrophilizing agents (e.g. Irgasurf™ HL560, TechMer PPM15560™, Bayhydur™ 304) as they are employed for PP textile fibers are particularly advantageous. Alternatively or additionally, polyethylene glycol (PEG, PEG400), the derivates thereof, hyaluronic acid, starch, oxethylated carbonic acid compounds, hydrophilic silicates, sucrose methacrylates, hydrophilized, aliphatic polyisocyanate based on hexamethylene diisocyanate (HDI) as well as diverse fibers and GMS (glycerin monostearate) as well as the derivates thereof are suitable. Further substances for providing hydrophilic characteristics are fatty alcohol phosphates as well as derivates of polyethylene oxide (PEO), in particular with hydroxyl terminal groups.

The mass content of the hydrophilizing and/or hygroscoping agent can be between 0.1% and 10%, in particular between 0.15 and 5% and preferably between 0.2% and 4% related to the mass of the composite material. For example, silica gel and Atmer (vegetable glycerol esters) with respective mass contents of about 2% can be used as hydrophilizing and/or hygroscoping agent, whereby a total mass content of 4% of hydrophilizing and hygroscoping agent, respectively, results. Alternatively, only 2% of silica gel or 2% of Atmer can for example also be used.

With the aid of the hydrophilizing and/or hygroscoping agent, the composite material can also be used in particularly dry environments with air humidity values below 20%. For activating or regenerating the antimicrobial efficacy, therein, it is sufficient to wet the surface of the composite material for example in weekly rhythm, for example to wipe it with a wet cloth.

By hygroscopic, it is to be understood that the composite material absorbs humidity at least on its surface or in the areas near the surface. For example, the composite material should absorb between 0.01 and 10 wt.-% of humidity in environments with <10% of relative air humidity. Particularly advantageous are 0.1 to 3% of equilibrium humidity, which usually appear after some minutes to hours.

The parameter values indicated in the documents for the definition of process and measurement conditions for the characterization of specific characteristics of the inventive subject matter are to be considered as encompassed by the scope of the invention also within the scope of deviations—for example due to measurement errors, system errors, weighing errors, DIN tolerances and the like.

The invention claimed is:

1. An antimicrobially effective composite material, wherein the antimicrobially effective composite material includes at least one molybdenum-containing inorganic compound incorporated into at least one further material, wherein the at least one further material forms a matrix;
  wherein the at least one molybdenum-containing inorganic compound:
    is present in a form of particles distributed within the matrix;
    is a compound of the molecular formula $A_zMoO_4$, where:
      A is a metal ion selected from the group consisting of K, Mg, Ca, Ag, Cu, Bi, V, Ti, and Zn,
      A is a cation with a charge of n+, and
      $n*z=+2$;
    has an average particle size of between 0.1 μm and 0.5 μm;
    does not elute or degrade as a result of contact with water; and
    does not elute or degrade to release metal cations;
  wherein the composite material includes at least one hydrophilizing and/or hygroscopic agent comprising silica gel, wherein the silica gel is present in a form of particles having a particle size distribution with an average particle diameter of between 0.1 μm and 25 μm;

wherein the mass content of the at least one hydrophilizing and/or hygroscopic agent relative to the total mass of the composite material is between 0.1% and 15% by weight;

wherein the mass content of the at least one hydrophilizing and/or hygroscopic agent is equal to one to two times the mass content of the at least one molybdenum-containing inorganic compound;

wherein the composite material, other than including the at least one molybdenum-containing inorganic compound, is otherwise free of elemental molybdenum, $MoO_2$, $MoO_3$, molybdenum carbide, molybdenum nitride, molybdenum silicide, molybdenum sulfide and/or molybdenum containing alloys, and wherein the composite material absorbs between 0.1 wt. % to 3 wt. % of humidity in environments with less than 10% of relative air humidity.

2. The composite material of claim 1, wherein
the at least one molybdenum-containing inorganic compound is doped or undoped, and
the at least one molybdenum-containing inorganic compound contains water of crystallization or is free of water of crystallization.

3. The composite material of claim 1, further comprising a mixed oxide of the formula $Mo_xW_{1-x}A_yO_z$, wherein $0<x<1$, $0<y<2$ and $2.0<z<3.0$ and A denotes $NH_4^+$ or a metal ion other than Mo and W.

4. The composite material of claim 3, wherein:
A of the mixed oxide is selected from the group consisting of Na, K, Mg, Ca, Ag, Cu, Bi, V, Ti and Zn, and
the mixed oxide is doped with an oxyfluoride, $WOF_4$, $WO_2F_2$, calcium fluoride and/or fluoroapatite.

5. The composite material of claim 1, wherein the mass content of the at least one molybdenum-containing inorganic compound relative to the total mass of the composite material is between 1.8% and 5.0% by weight.

6. The composite material of claim 1, wherein the at least one molybdenum-containing inorganic compound is at least partially coated and/or agglomerated with the at least one hydrophilizing and/or hygroscoping agent.

7. The composite material of claim 1, wherein the at least one further material comprises at least one organic polymer, silicone, or both.

8. The composite material of claim 1, wherein the composite material is configured as a layer composite, fiber composite, particle composite or penetration composite.

9. The composite material of claim 1, wherein the composite material is present in the form of a solution, suspension, or dispersion.

10. The composite material of claim 1, wherein the at least one molybdenum-containing inorganic compound is present in a region of the surface of the composite material, distributed within the composite material, or both.

11. The composite material of claim 1, wherein the at least one hydrophilizing and/or hygroscopic agent is between 0.1% and 0.2% by weight, and wherein the mass content of the at least one hydrophilizing and/or hygroscopic agent is equal to two times the mass content of the at least one molybdenum-containing inorganic compound.

12. The composite material of claim 1, wherein the at least one further material comprises a hydrophobic polymer.

13. The composite material of claim 1, wherein the matrix of the at least one further material comprises a solid matrix.

14. The composite material of claim 1, wherein the matrix of the at least one further material comprises a liquid matrix.

15. The composite material of claim 1, wherein the composite material is present as a solid.

* * * * *